United States Patent [19]
Friberg et al.

[11] Patent Number: 5,201,309
[45] Date of Patent: Apr. 13, 1993

[54] BREATHING AID FOR LARYNGOTOMY TRACHEOSTOMY PATIENTS

[75] Inventors: Roland Friberg, Sollentuna; Inge Blomquist, Vaggeryd, both of Sweden

[73] Assignees: Gillis Andersson, Danderyd; Bror Palmcrantz, Vaellingby, both of Sweden

[21] Appl. No.: 795,566

[22] Filed: Nov. 21, 1991

[30] Foreign Application Priority Data

Nov. 22, 1990 [SE] Sweden .................... 9003720

[51] Int. Cl.⁵ .................... A61M 16/04; B65D 55/16
[52] U.S. Cl. .................... 128/207.14; 128/204.17; 128/205.12; 215/306; 220/375
[58] Field of Search .................... 128/207.14, 207.15, 128/207.16, 207.17, 204.17, 205.12; 215/306; 220/375, 339

[56] References Cited

U.S. PATENT DOCUMENTS

| | | | |
|---|---|---|---|
| 3,137,299 | 6/1964 | Tabor | 128/207.16 |
| 4,022,352 | 5/1977 | Pehr | 220/375 X |
| 4,029,202 | 6/1977 | Lasich et al. | 220/375 X |
| 4,325,366 | 4/1982 | Tabor | 128/207.16 |
| 4,755,356 | 7/1988 | Robbins et al. | 215/306 X |

FOREIGN PATENT DOCUMENTS

| | | | |
|---|---|---|---|
| 387220 | 9/1990 | European Pat. Off. | 128/207.15 |
| 462367 | 6/1990 | Sweden . | |
| 2214089 | 8/1989 | United Kingdom | 128/207.16 |
| 91-05579 | 5/1991 | World Int. Prop. O. | 128/207.14 |

*Primary Examiner*—V. Millin
*Assistant Examiner*—Raleigh W. Chiu
*Attorney, Agent, or Firm*—Finnegan, Henderson, Farabow, Garrett & Dunner

[57] ABSTRACT

A breathing aid for laryngotomoy tracheostomy patients includes a filter house made from plastics material, which is provided to receive a replaceable filter and which is made in one piece with a cover having perforations, the cover being provided to close the filter house via a flexible integral hinge strip. The breathing aid includes a hood applicable upon the cover and having a downwardly directed suction channel through which the inhaled air has to pass before it reaches the filter, the hood having a recess which by cooperation with the hinge strip guarantees the correct orientation of the hood and holds it in this position. The filter house can be secured to an adhesive foil which has rectangular or square shape and the filter house is so orientated in relation to the foil that the pivot axis of the hinge will be parallel to one of the sides of the foil.

12 Claims, 1 Drawing Sheet

BREATHING AID FOR LARYNGOTMY TRACHEOSTOMY PATIENTS

BACKGROUND OF THE INVENTION

1. Field of the Invention

This invention refers to a breathing aid for laryngotomy tracheostomy patients.

2. Description of Prior Art

For patients of this kind it is very important that the air inhaled through the larynx as far as possible will have the same properties as the air which normally may pass through the nose and pharynx. For this purpose aids have been developed which filter the air and moisten it. Further it is important that these aids will enable the patient to take a shower bath without risk, to be out in the open air also in rainy weather, and so forth.

By SE 462 367 it is previously known to arrange a so called preheating shield which may be slid onto the filter house or the cover thereof and which when applied will effect that the inhaled air will consist of the air column which is pre-warmed by the heat from the human body and which raises from the chest and lower neck region of the patient. It may be emphasized that a breathing aid which is intended for use by tracheostomy patients in addition to said filtering and moistening function should include a valve making it possible for the patient to talk. The mentioned SE patent describes such a breathing aid having, however, no valve for tracheostomy patients.

The known breathing aids are encumbered with some other serious drawbacks. One of them is that the filtering house has to be provided with a separate cover which may be difficult to apply and which easily may be lost. A second drawback is that the heating shield—which enables the patient to take shower baths without the risk of inhaling water—easily may be displaced from its initial correct position and/or may be erroneously applied such that the sucking channel thereof will be wrongly directed. This, of course, entails a considerable risk for the patient as inhaling water or air strongly mixed with water may bring forth serious damage.

SUMMARY OF THE INVENTION

The object of the invention thus has been to eliminate said drawbacks and to achieve these and further objects the invention has following characteristics.

The breathing aid for laryngotomy tracheostomy patients of the present invention includes a filter house which is provided to be applied near to and in communication with the opening which is provided in the throat of the patient and which is provided to receive a replaceable filter unit through which the breathing air passes and further a cover with perforations. The cover holds the filter unit in place and by the opening of which the filter unit may be removed for replacement and in which a heat shield is connectable with the filter house respectively the cover thereof such that only air which has passed through a downwardly directed channel in said heat shield may be breathed. Importantly, the filter house is made in one piece with the cover by means of a flexible strip which connects the filter house and the cover. The strip serves as a hinge for swinging the cover from an open position to a closing position and the cover and the heat shield location have interacting locating means for the correct registering of the heat shield in relation to the filter house and locking it thereto.

Preferably, the locating means includes the strip forming the hinge and a recess formed in the heat shield, the recess being located at a predetermined position in relation to the suction channel of the heat shield. The unit consisting of filter house, cover and hinge can be made from plastics material such as polypropene.

It is also preferred that the breathing aid has a thin and soft foil made from synthetic material which has an opening for communication with the opening in the throat of the patient and which on one of its sides has an adhesive layer which, preferably, initially is covered by a protection sheet. The adhesive layer is provided to secure the foil to the patient's neck while the opposite side thereof holds the filter house. The filter house preferably is cylindrically shaped and has an end wall connected to the foil, the end wall having an opening communicating with the opening of the foil and, in the portion thereof which is opposite to the end wall, is open and may be covered by the cover which has a flange portion embracing the filter house. The filter house further has a wall portion for covering the mouth portion of the filter house, which further wall portion serves to keep the filter unit in the filter house and which further has a number of holes through which the breathing air may pass.

It is further preferred that the strip which connects the filter house and the cover extends from a part of the filter house which is located at an axial distance from the mouth of the filter house. Also, the opening in the end wall of the filter house preferably is bridged by a narrow, curved rib the highest point of which is located inside the filter house.

It is still further preferred that the foil is substantially rectangular or square end that the filter house is secured to it in such a manner that the hinge will have a pivot axis which is parallel to one of the sides of the foil.

It is also further preferred that snap means are provided to arrest the cover in that position in which it covers the opening of the filter house and/or to arrest the heat shield in that position in which it is applied upon the cover.

And it is still further preferred that the heat shield includes an annular portion provided to grasp a correspondingly shaped annular portion of the cover. The recess is provided in the first mentioned annular portion and in a part thereof which is located behind the suction channel of the heat shield.

BRIEF DESCRIPTION OF THE DRAWING

The accompanying drawing illustrates an exemplary embodiment of the invention. In the drawing.

DESCRIPTION OF THE PREFERRED EMBODIMENT

As initially has been pointed out the present invention may be used with breathing aids with return valve as well as with such aids having no such valve but since the general design in both cases will be similar only a breathing aid for laryngotomy patients will be described here.

Figure 3:
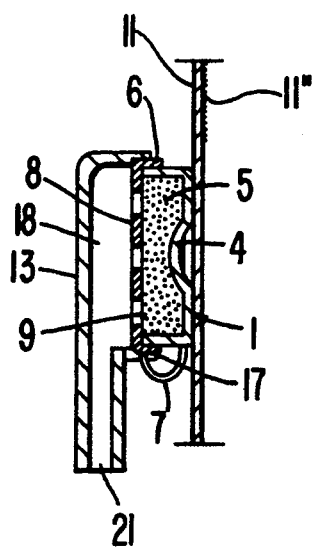
FIG. 3 is a section after line III—III in FIG. 1 with applied heating shield while FIG. 4 finally is a section after line IV—IV in FIG. 1 with applied heating shield.

The breathing aid illustrated on the drawing includes a filter house, generally designated 1, which preferably is cylindrical and open in one direction while it in the opposite direction has a wall portion 2, which has an opening 3 bridged by a rib 4, which as appears from FIG. 3 is curved so that the central portion thereof will be situated at a distance from the level of the wall portion 2 This rib serves to prevent that the filter unit 5, which the filter house is provided to house with the central portion thereof, from being sucked into the stoma. As a result of the use of the curved shape, the rib may be selected so thin that a tube when necessary may be introduced in the stoma via the opening 3.

The filter house which preferably is made from plastic material with a so called hinge-effect such as polypropylene, is made in one piece with a cover 6 via a flexible strip 7, which as appears from FIG. 3 extends from the filter house intermediate the end surfaces thereof. The cover 6 consists of a substantially planar wall 8 covering the filter house opening and in which a number of through holes or perforations 9 are provided and an annular flange portion 10, which is intended to embrace the mouth portion of the filter house when the cover is applied. It is understood that the cover in its active, shown position will hold the filter unit in the filter house. The filter unit 5 of the illustrated embodiment consists of a circular piece which with friction fits in the filter house. It is understood that the filter house and the cover may be provided with interacting snapping parts to hold the cover in the position in which it embraces the mouth of the filter house but that such a holding action may also be attained by providing the cover and the filter house with interacting tapered portions for holding the cover by friction and that combinations of said holding systems may be contemplated.

The breathing aid has the same function as the aids previously known, i.e., the air is filtered by passing the filter unit and is moistened due to the fact that the exhaled air when passing out through the filter by condensation deposits part of its moisture to the filter such that this moisture, when inhaling takes place, will be supplied to the air coming from outside.

Figure 4:
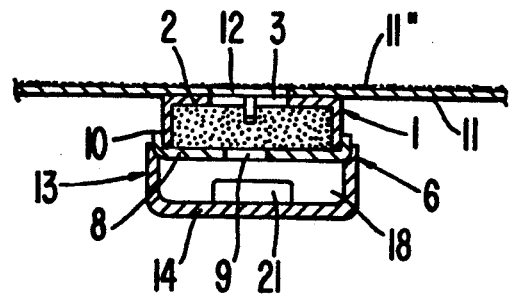

In the illustrated embodiment the filter house 1, for example, by bonding secured to one side of a thin and flexible foil 11, preferably made from a suitable synthetic material said foil at the illustrated embodiment having a substantially rectangular or square shape and which has an opening 12 (See FIG. 4) which is in register with the opening 3 in the end wall 2 of the filter house. At the opposite side thereof the foil has an adhesive layer 11" which at the time of delivery is covered by a protection foil to be removed. By aid of the adhesive layer 11" thereof the foil and consequently also the filter house is fastened to the neck of the patient in such a manner that the opening 12 thereof will be in register with the opening in the throat region respectively with a catheter or the like introduced in said opening. At the same time it has to be checked that the strip serving as a hinge 7 will have a certain orientation which in the illustrated embodiment means that the strip 7 is to be situated at the lower part of the filter house which automatically occurs when the upper edge 11' of the foil extends in a horizontal direction. It is understood that replacement of filter unit 5 easily may be carried out by the patient himself in such a construction since it is only necessary for him to grasp the cover and swing it downwardly, remove the used filter unit replace it with a new one and again swing up the cover to its shown, active position.

As has been initially pointed out it is further important that the patient is offered the possibility to wash, take a shower bath and the like without risk and for this purpose and/or for the purpose of attaining a pre-heating of the inhaled air a so called heating shield is provided. In the shown embodiment a hood 13 is provided with an end wall 14, the annular part 15 thereof at the opening of the hood having an inner diameter which substantially corresponds to the outer diameter of the cover 6 but which in its portion adjacent to the end wall has a smaller inner diameter such that in the inner portion of the hood is generated a circumferential flange portion 16.

Figure 1:
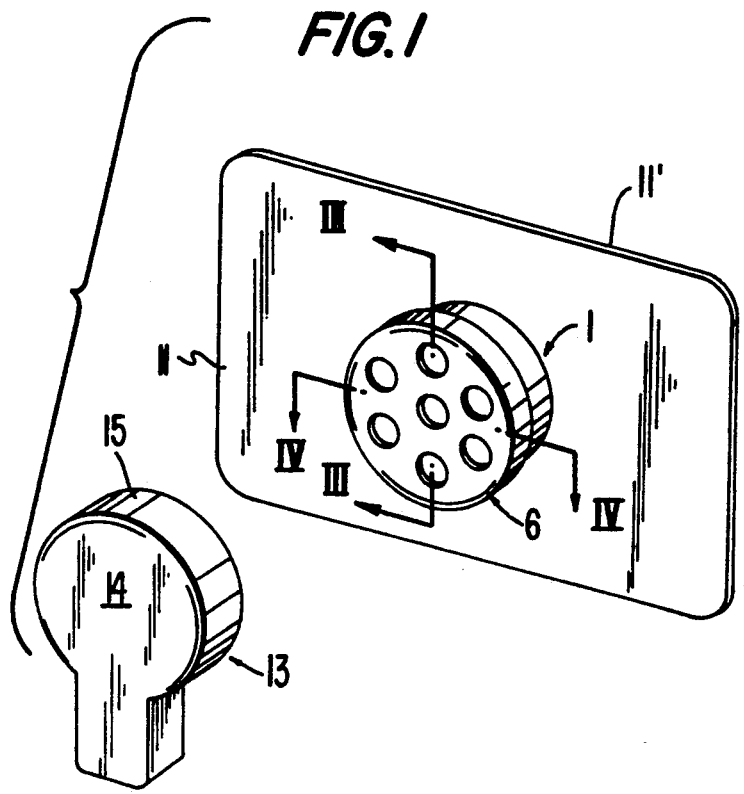
FIG. 1 shows in perspective a breathing aid intended for laryngotomy patients as well as for tracheostomy patients and includes a so called heating shield suited for the purpose.
Figure 2:
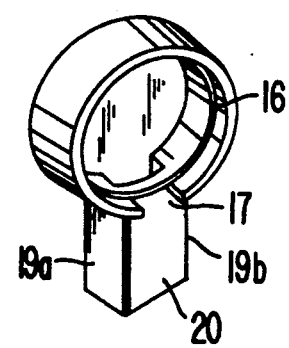
FIG. 2 shows, also in perspective, the heating shield in another perspective than in FIG. 1.

In the lower part of the hood (See FIG. 2), there is provided a recess 17, which is dimensioned in such a manner that the strip 7 which connects the filter house 1 and the cover 6 fits therein when the hood is slid onto the cover. Since the flange 16 of the hood will abut against the outer side of the cover a chamber 18 will be generated between the end wall 14 and the hood and the cover. Said end wall is, as especially appears from FIG. 1 and FIG. 3, extended downwardly and by side walls 19a, 19b connected thereto and a rear wall 20 preferably parallel to the end wall a channel 21 will be generated which communicates with the chamber 18 and which is downwardly directed. When the hood is in place only air coming from below will be sucked in.

Since the strip 7 serving as a hinge will be positively and correctly orientated when the aid is applied to the patient's throat and since the recess 17 has a positive orientation relative to the channel 21 through which air is sucked in when the heat shield is in place, the present invention provides that this channel will be correctly orientated and that the orientation may not be dislocated for instance through an accidental movement of the hand or the like.

It is understood that the heat shield or the hood also may be provided with snapping devices or the like to ensure the fastening of the hood in cooperation with complementary means at the filter house and/or the cover. In the shown embodiment the cover is intended to be swung downwardly when the filter is changed and this is seen to be the most convenient design but nothing prevents that the cover may be swung away in another direction, for instance, laterally. In such a case the recess 17 however has to be appropriately orientated in a corresponding degree. If one wishes to place the strip 7 at the upper side of the filter house it may however be desirable to surround the recess of the hood with wall portions which completely prevents water from entrance into the hood from above. As initially pointed out the invention may also be used with so called spaced valves and it may also be pointed out that it, of course, may be used with other fastening methods than the method shown with an adhesive member, for instance when it has to be mounted upon a tube for medical use. The filter house will then, of course, be designed according to SE 462 367 with an attachment flange instead of an adhesive foil. It is also possible to provide the heat shield with alternative recesses preferably in the shape of breaking recesses so that the swing direction of the cover may be varied as desired.

We claim:

1. A breathing aid for laryngotomy tracheostomy patients of the type having a replaceable filter unit, the aid comprising a filter house adapted to be applied near to and in communication with the opening which is provided in the throat of the patient and which is adapted to receive the replaceable filter unit through which the breathing air passes; a cover with perforations, said cover adapted to close said filter house and hold the filter unit in place and by the opening of which the filter unit may be removed for replacement; and a heat shield releasably connected to the cover, said heat shield having a directed channel and being adapted to direct only air which has passed through said directed channel to pass through the perforations, wherein the filter house is made in one piece with the cover by means of a flexible strip which connects the filter house and the cover to comprise a filter house unit, said strip serving as a hinge for swinging the cover from an open position to a closing position, and wherein said filter house unit and the heat shield have interacting location means for the correct registering of the heat shield in relation to said filter house.

2. The breathing aid as claimed in claim 1, wherein said interacting location means comprises the strip forming the hinge and a recess formed in the heat shield, said recess being located at a predetermined position in relation to the directed channel of the heat shield.

3. The breathing aid as claimed in any one of claims 1-2, wherein the heat shield comprises an annular portion adapted to grasp a correspondingly shaped annular portion of the cover, wherein the recess is provided in the first mentioned annular portion.

4. The breathing aid as claimed in claim 1 wherein said interacting location means also are for locking the heat shield to the filter house unit.

5. The breathing aid as claimed in claim 1, wherein the filter house unit is made from a plastics material having a hinge effect.

6. The breathing aid as claimed in claim 5 wherein said plastic material is polypropylene.

7. The breathing aid as claimed in claim 1, further including a thin and soft foil which has an opening for communication with the opening in the throat of the patient and which on one of its sides has an adhesive layer provided to secure the foil to the patient's neck and which on the opposite side thereof is connected to the filter house, wherein the filter house is cylindrically shaped and has an end wall connected to the foil, said end wall having an opening communicating with the opening of the foil and has an open end opposite to said end wall, and wherein the cover has a flange portion adapted to embrace the filter house open end and further has a wall portion for covering the filter house open end and which serves to keep the filter unit in the filter house and which further has a plurality of holes through which the breathing air may pass.

8. The breathing aid as claimed in claim 4 wherein the foil is substantially rectangular and the filter house is connected to said foil such that the hinge will have a pivot axis which is parallel to one of the sides of the foil.

9. The breathing aid as claimed in any one of claims 1-7, wherein the filter house further includes a narrow curved rib, the opening in the end wall of the filter house being bridged by said narrow curved rib, the highest point of which is located inside the filter house.

10. The breathing aid as claimed in claim 1, wherein the strip which connects the filter house and the cover extends from a part of the filter house which is axially spaced from the open end of the filter house.

11. The breathing aid as claimed in claim 1, further including snap means for arresting the cover in that position in which it covers the open end of the filter house.

12. The breathing aid as claimed in claim 1, further including snap means for arresting the heat shield in that position in which it is connected to said cover.

* * * * *

UNITED STATES PATENT AND TRADEMARK OFFICE
CERTIFICATE OF CORRECTION

PATENT NO. : 5,201,309
DATED : April 13, 1993
INVENTOR(S) : ROLAND FRIBERG et al.

It is certified that error appears in the above-identified patent and that said Letters Patent is hereby corrected as shown below:

Claim 9, col. 6, line 24, "1-7" should be --1, 2, 5, and 7--.

Signed and Sealed this

Twenty-second Day of March, 1994

Attest:

BRUCE LEHMAN

Attesting Officer     Commissioner of Patents and Trademarks